United States Patent
Umekawa et al.

(10) Patent No.: US 9,724,049 B2
(45) Date of Patent: Aug. 8, 2017

(54) RADIOTHERAPY SYSTEM

(71) Applicant: HITACHI, LTD., Tokyo (JP)

(72) Inventors: Toru Umekawa, Tokyo (JP); Kazuo Hiramoto, Tokyo (JP); Rika Baba, Tokyo (JP); Toshie Sasaki, Tokyo (JP); Yoshihiko Nagamine, Tokyo (JP); Shinichi Shimizu, Sapporo (JP); Seishin Takao, Sapporo (JP); Naoki Miyamoto, Sapporo (JP); Taeko Matsuura, Sapporo (JP); Kikuo Umegaki, Sapporo (JP)

(73) Assignee: Hitachi, Ltd., Tokyo (JP)

( * ) Notice: Subject to any disclaimer, the term of this patent is extended or adjusted under 35 U.S.C. 154(b) by 87 days.

(21) Appl. No.: 14/450,546

(22) Filed: Aug. 4, 2014

(65) Prior Publication Data

US 2015/0036793 A1    Feb. 5, 2015

(30) Foreign Application Priority Data

Aug. 5, 2013    (JP) .................................. 2013-162656

(51) Int. Cl.
| | |
|---|---|
| *A61B 6/00* | (2006.01) |
| *A61B 6/03* | (2006.01) |
| *A61N 5/10* | (2006.01) |

(52) U.S. Cl.
CPC ............ *A61B 6/032* (2013.01); *A61B 6/5294* (2013.01); *A61B 6/541* (2013.01); *A61N 5/1049* (2013.01);
(Continued)

(58) Field of Classification Search
CPC .......... A61N 5/1049; A61N 2005/1061; A61N 5/103; A61N 5/1048; A61N 5/1069
See application file for complete search history.

(56) References Cited

U.S. PATENT DOCUMENTS

| | | | |
|---|---|---|---|
| 2004/0218719 A1 | 11/2004 | Brown et al. | |
| 2007/0211857 A1* | 9/2007 | Urano | A61N 5/1049 378/65 |
| 2012/0106704 A1* | 5/2012 | Maurer, Jr. | G06F 19/3481 378/65 |

FOREIGN PATENT DOCUMENTS

| | | |
|---|---|---|
| EP | 1 683 545 A2 | 7/2006 |
| EP | 2 578 271 A1 | 4/2013 |

(Continued)

OTHER PUBLICATIONS

European Patent Office; European Search Report in European patent application No. 14179862.6; mailed Jan. 8, 2015; 6 pages.

(Continued)

*Primary Examiner* — Hoon Song
(74) *Attorney, Agent, or Firm* — Mattingly & Malur, PC (57) ABSTRACT

A radiotherapy system acquires an image which is necessary for positioning of a patient for radiation treatment and enables grasping of a positional relationship of a target in a treatment radiation irradiated state, a radiation passing area and a critical organ. An X-ray imaging device is attached to the rotatable support device and configured to apply X-rays to the subject from plural directions while rotating around the subject to perform X-ray imaging. A target recognizing device recognizes a three-dimensional position of the target in the subject from X-ray images acquired by the X-ray imaging device; and CT image generating devices are configured to select, from the X-ray images acquired by the X-ray imaging device, the images in which the position of the target recognized by the recognizing device satisfies the treatment radiation irradiation condition for the motion tracking treatment to perform image reconstruction and generate a cone beam CT image.

8 Claims, 7 Drawing Sheets

(52) U.S. Cl.
CPC .... *A61N 5/1081* (2013.01); *A61N 2005/1061* (2013.01)

(56) References Cited

FOREIGN PATENT DOCUMENTS

| | | |
|---|---|---|
| JP | 2004-097646 A | 4/2004 |
| JP | 3746747 B2 | 12/2005 |
| JP | 2010-505562 A | 2/2010 |
| JP | 4499087 B2 | 4/2010 |
| JP | 2010-183976 A | 8/2010 |
| WO | 2008/043378 A1 | 4/2008 |
| WO | 2011/039624 A2 | 4/2011 |

OTHER PUBLICATIONS

Japanese Office Action received in corresponding Japanese Application No. 2013-162656 dated Apr. 11, 2017.

\* cited by examiner

IN THE CASE OF INTERCEPTING IRRADIATION

FIG. 5B

RADIOTHERAPY SYSTEM

BACKGROUND OF THE INVENTION

1. Field of the Invention

The present invention relates to a radiotherapy system having a motion tracking device for recognizing and tracking the position of a target.

2. Description of the Related Art

For radiotherapy of irradiating a target in the body with treatment radiation, there has been described in, for example, Japanese Patent No. 3746747 (hereinafter, referred to as Patent Document 1), a radiotherapy system which uses a motion tracking device for recognizing a target position in a body and applies the treatment radiation on the basis of the recognized target position. The purpose of recognizing the target position is to irradiate a target as in the treatment plan even when there is a movement of the target due to respiration or the like.

As an irradiation method of the treatment radiation using the motion tracking device, there are intercepting irradiation in which irradiation is performed only where the target position coincides with a plan, and pursuing irradiation in which the direction of the treatment radiation is changed according to the movement of the target position. Patent Document 1 discloses an example of the pursuing irradiation. In any case, in order to correctly reproduce a dose distribution in a patient's body, there is a need to correctly position a patient (subject) inclusive of not only the target position but also peripheral organs. This is because when a substance in the passing area of radiation changes, a dose reaching the target changes. This is also done to avoid entering of a critical organ not to be irradiated with radiation into a radiation passing area.

In order to correctly position the patient, the positional relationship of the target in the patient's body, the radiation passing area and the critical organ or the like is required to be grasped. To this end, a three-dimensional X-ray CT image (computed tomographic image) is used. Patent Document 1 has described that a cone beam CT apparatus is used which performs imaging using an X-ray imaging device installed in a rotatable support device of the radiotherapy system.

Further, there is known Japanese Patent No. 4499087 (hereinafter, referred to as Patent Document 2) as a technology for photographing or capturing an image that enables the positional relationship of a target moved due to respiration, a radiation passing area and a critical organ to be grasped precisely in cone beam CT. Patent Document 2 describes: "Means for performing a cone beam CT scan to obtain a plurality of planar projection images of a patient, means for determining a respiration cycle of each projection image using the in-projection image feature of each of a plurality of projection images, and means for directly applying a respiration correlated technique to the projection image, on the basis of the determined respiration cycle."

SUMMARY OF THE INVENTION

Since such a cone beam CT apparatus as described in Patent Document 1 performs imaging while rotating using the rotatable support device of the radiotherapy system, the imaging is generally done with one rotation or so per minute and takes longer than the respiration cycle, about 3 seconds or so. Fluoroscopic images acquired in a cycle longer than breathing include images of various states of expiration and aspiration. A CT image three-dimensionally reconstructed from those fluoroscopic images becomes an average image of various states. That is, the CT image is blurred. This image becomes difficult in precisely grasping the positional relationship of the target, the radiation passing area and the critical organ. It is therefore inappropriate as a positioning image.

When the method of Patent Document 2 is used, a CT image lying within the range of a breathing phase can be acquired by performing image reconstruction using the projection images correlated to the respiration. If the phase range is sufficiently small, a CT image is obtained in which the movements of the target, the radiation passing area and the critical organ are suppressed to be sufficiently low. This becomes an image that makes it possible to precisely grasp the positional relationship.

In Patent Document 2, however, since the respiration cycle of the fluoroscopic image is determined using the feature (e.g., the position of the diaphragm) in the fluoroscopic image, the state limited by the above breathing phase does not necessarily coincide with the state (treatment state) in which the treatment radiation is applied. For example, in the intercepting irradiation, a treatment beam is irradiated only when a target is placed in a specific position, but the state of the target being in the specific position and the state of the target being in breathing phase do not necessarily coincide with each other.

Thus, in the technology of Patent Document 2, it is not possible to acquire the image which is necessary for the positioning of the patient for the radiation treatment and enables the grasping of the positional relationship of the target in the irradiated state of the treatment radiation, the radiation passing area and the critical organ. Consequently, a problem arises in that precise patient positioning as in treatment plan cannot be performed.

An object of the present invention is to provide a radiotherapy system capable of acquiring an image which is necessary for positioning of a patient for radiation treatment and enables grasping of a positional relationship of a target in a treatment radiation irradiated state, a radiation passing area and a critical organ.

In order to solve the above problem, the present invention includes a plurality of means for solving the above problem, but the following is an example thereof. A radiotherapy system is provided which comprises a couch for supporting a subject, a rotatable support device disposed to surround the couch, a treatment radiation irradiating device attached to the rotatable support device, and a treatment radiation control device that controls the treatment radiation irradiating device so as to irradiate the subject when the position of a target in the subject satisfies a treatment radiation irradiation condition for motion tracking treatment. The radiotherapy system further comprises an X-ray imaging device attached to the rotatable support device and configured to apply X-rays to the subject from a plurality of directions while rotating around the subject to perform X-ray imaging, a target recognizing device that recognizes a three-dimensional position of the target in the subject from X-ray images acquired by the X-ray imaging device, and a first CT image generating apparatus configured to select the images in which the position of the target recognized by the target recognizing device satisfies the treatment radiation irradiation condition for the motion tracking treatment, out of the X-ray images to perform image reconstruction and generates a first cone beam CT image.

With such features, since the images in which the position of the target recognized by the target recognizing device satisfy the treatment radiation irradiation condition for the motion tracking treatment are selected out of the X-ray images obtained by the X-ray imaging device to generate the first cone beam CT image, the subject in the treatment radiation irradiated state can be brought into three-dimensional CT imaging (visualization). It is thus possible to acquire an image which enables grasping of a positional relationship of a target in a treatment radiation irradiated state, a radiation passing area and a critical organ which are necessary for patient's positioning for radiation treatment.

Also, the present invention has also a feature in that the treatment radiation irradiation conditions are set for a plurality of positions, and the first CT image generating apparatus selects images in which the target position satisfy the respective set conditions for the plural positions and generates a plurality of reconstructed cone beam CT images.

With such features, it is possible to obtain an image which enables grasping of a positional relationship of a target, a radiation passing area and a critical organ in plural states relative to the movement of the target.

Further, the present invention has also a feature in that the X-ray imaging device and the target recognizing device serve as an X-ray imaging device and a target recognizing device for the motion tracking treatment, and the treatment radiation control device determines on the basis of the position of the target recognized by the target recognizing device whether or not the position of the target in the subject satisfies the treatment radiation irradiation condition for the motion tracking treatment.

With such features, when the motion tracking treatment is performed after the precise positioning of the patient, the motion tracking treatment is carried out on the basis of the same treatment radiation irradiation condition, thereby enabling motion tracking treatment with good precision.

Furthermore, the present invention has also a feature in that the radiotherapy system further includes a second CT image generating apparatus that performs image reconstruction using all images without selection of any image from the X-ray images acquired by the X-ray imaging device to generate a second cone beam CT image, a first subject positional displacement amount determining device that compares the second cone beam CT image and the image of the treatment plan to determine an amount of positional displacement of the subject, and a first target position correcting device that corrects the position of the target recognized by the target recognizing device on the basis of the positional displacement amount determined by the first subject positional displacement amount determining device, and that the first CT image generating apparatus selects, out of the X-ray images acquired by the X-ray imaging device, the images in which the position of the target corrected by the first target position correcting device satisfies the treatment radiation irradiation condition for the motion tracking treatment acquired by the X-ray imaging device to perform image reconstruction and generates the first cone beam CT image.

With such features, it is possible to perform on software (arithmetic processing) not only cone beam CT imaging of the subject in the treatment state but also coarse positioning of the subject prior to the cone beam CT imaging. High-accuracy positioning becomes possible compared with the conventional coarse positioning before the cone beam CT imaging performed using marking on the surface of the subject or the position of a marker seen through by the X-ray imaging device, etc.

According to the present invention, since a subject in a treatment radiation irradiated state can be brought into three-dimensional CT imaging, it is possible to obtain an image that enables grasping of a positional relationship of a target in the treatment radiation irradiated state, a radiation passing area and a critical organ, thus enabling precise positioning of a patient as in the treatment plan.

Also, according to the present invention, when the motion tracking treatment is performed after the precise positioning of the patient, the motion tracking treatment is carried out on the basis of the same treatment radiation irradiation condition, thereby enabling motion tracking treatment with good precision.

Further, according to the present invention, it is possible to perform on software (arithmetic processing) not only cone beam CT imaging of the subject in the treatment state but also coarse positioning of the subject prior to the cone beam CT imaging. High-accuracy positioning becomes possible compared with the conventional coarse positioning before the cone beam CT imaging performed using marking on the surface of the subject or the position of a marker seen through by the X-ray imaging device, etc.

DESCRIPTION OF THE PREFERRED EMBODIMENTS

First Embodiment

A first embodiment of the present invention will be described using FIGS. 1A, 1B and 2, and FIGS. 5A and 5B.

Figure 1A:
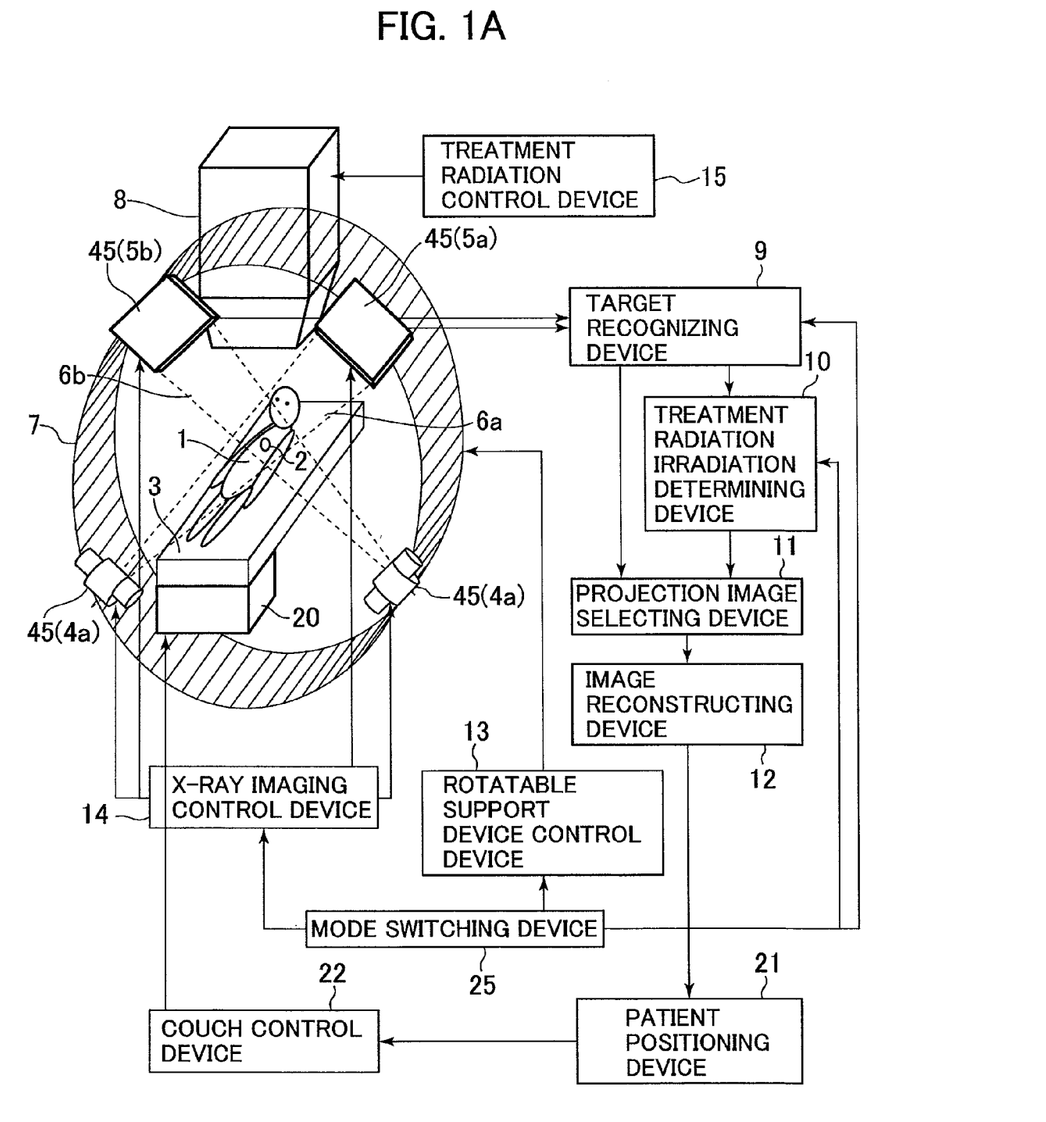
FIG. 1A is a diagram showing a schematic configuration of a radiotherapy system according to a first embodiment of the present invention, and a diagram showing a state when a cone beam CT imaging mode is selected and the radiotherapy system is operated as a patient positioning system.
Figure 1B:
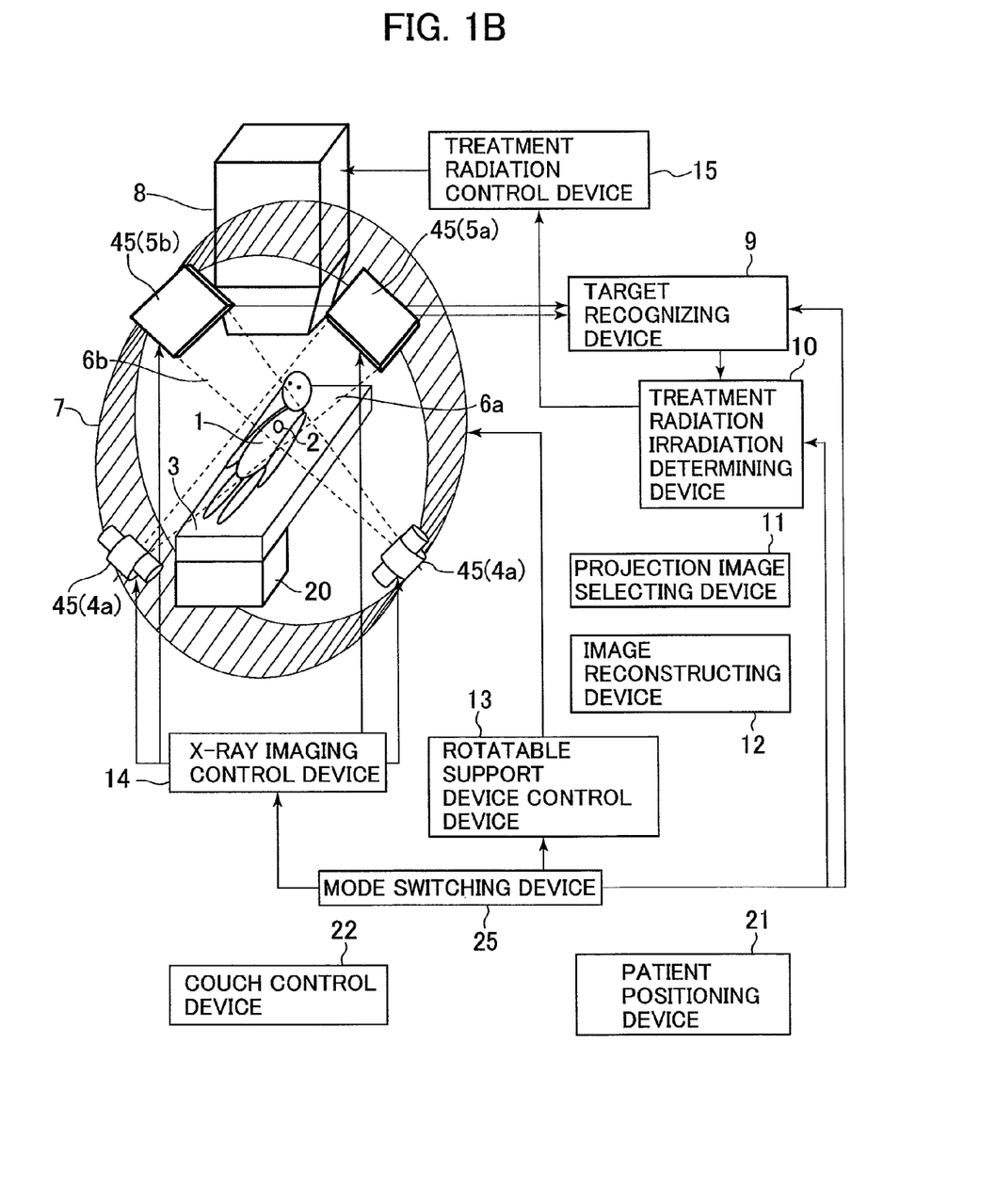
FIG. 1B is a diagram showing the schematic configuration of the radiotherapy system according to the first embodiment of the present invention, and a diagram showing a state when a motion tracking treatment mode is selected and the radiotherapy system is operated as a motion tracking treatment system.

FIGS. 1A and 1B are diagrams showing a schematic configuration of a radiotherapy system according to the present embodiment. FIG. 1A shows a state when a cone beam CT imaging mode is selected and the radiotherapy system is operated as a patient positioning system. FIG. 1B shows a state when a motion tracking treatment mode is selected and the radiotherapy system is operated as a motion tracking treatment system.

The radiotherapy system according to the present embodiment has a couch 3 that supports a subject (patient) 1, a rotatable support device 7 that surrounds the couch 3, an X-ray imaging device 45 attached to the rotatable support device 7 so as to rotate integrally with the rotatable support device 7, a treatment radiation irradiating device 8 attached to the rotatable support device 7 so as to rotate integrally with the rotatable support device 7, and a couch driving device 20 that drives the couch 3.

Further, the radiotherapy system has, as means for controlling the above respective devices, a target recognizing device 9, a treatment radiation irradiation determining device 10, a projection image selecting device 11, an image reconstructing device 12, a rotatable support device control device 13, an X-ray imaging control device 14, a treatment radiation control device 15, a patient positioning device 21 (subject positioning device), a couch control device 22, and a mode switching device 25.

The X-ray imaging device 45 has two pairs of X-ray tubes 4a and 4b and X-ray detectors 5a and 5b which are attached to the rotatable support device 7 so as to rotate integrally with the rotatable support device 7 and take X-ray images from two directions of a target 2 in the subject 1 lying on the couch 3. The X-ray tubes 4a and 4b respectively irradiate cone beam-like X-rays 6a and 6b, on the basis of imaging signals transmitted by the X-ray imaging control device 14. The cone beam-like X-rays 6a and 6b are transmitted through the subject 1 and detected by the X-ray detectors 5a and 5b respectively. The X-ray detectors 5a and 5b generate X-ray fluoroscopic images, on the basis of the passing amounts of X-rays. The generated two images are transmitted to the target recognizing device 9.

The X-ray imaging device 45 is also used in cone beam CT imaging for patient positioning at the start of treatment in addition to being used in motion tracking at the time of treatment. The mode switching device 25 is provided to change control of the X-ray imaging device 45 to the motion tracking treatment mode and the cone beam CT imaging mode. When the mode is switched by the mode switching device 25, a mode signal is communicated to the target recognizing device 9, the treatment radiation irradiation determining device 10, the rotatable support device control device 13 and the X-ray imaging control device 14 to switch the control.

When the cone beam CT imaging mode is selected by the mode switching device 25, a rotation signal is transmitted from the rotatable support device control device 13 to the rotatable support device 7 to rotate the X-ray imaging device 45 (X-ray tubes 4a and 4b and X-ray detectors 5a and 5b). The X-ray imaging device 45 intermittently or continuously performs X-ray imaging while rotating to thereby acquire bidirectional X-ray fluoroscopic images as seen from multiple directions (at a large number of angular positions of the rotatable support device 7) of the subject 1. Further, the X-ray imaging device 45 is capable of recording the angle of the rotatable support device 7 for every image photography and discriminating whether or not X-ray fluoroscopy is imaged from any direction.

The target recognizing device 9 recognizes a target projection position from the two images (bidirectional images) transmitted from the X-ray imaging device 45 and determines a three-dimensional position (three-dimensional coordinate values) of the target 2 from the target projection position by backprojection calculation. Upon recognition of the target 2, template matching (image recognition processing) is used in which a similar area is searched from the fluoroscopic images with the preset X-ray fluoroscopic images of the target 2 as templates. The target recognizing device 9 transmits information about the determined three-dimensional position of the target 2 to the treatment radiation irradiation determining device 10. Further, the target recognizing device 9 transmits the recognized X-ray fluoroscopic images to the projection image selecting device 11.

The treatment radiation irradiation determining device 10, the projection image selecting device 11 and the image reconstructing device 12 function as a first CT image generating apparatus which selects each image in which the position of the target recognized by the target recognizing device 9 satisfies a treatment radiation irradiation condition for motion tracking treatment to perform image reconstruction and thereby generates a first cone beam CT image. Its details will be described below.

The treatment radiation irradiation determining device 10 determines whether or not the transmitted target position satisfies the preset treatment radiation irradiation condition. The treatment radiation irradiation condition corresponds to an irradiation permission area for intercepting irradiation where the motion tracking treatment in the motion tracking treatment mode is for intercepting irradiation. Whereas, the treatment radiation irradiation condition corresponds to an irradiation permission area for the pursuing irradiation where the motion tracking treatment is for pursuing irradiation. In these motion tracking therapies, the treatment radiation irradiation condition is set to take a range of ±2 mm from the target position of the treatment plan, for example. Incidentally, in the cone beam CT imaging mode, the subject 1 is required to be positioned roughly in advance in a treatment radiation irradiation state. As is known, a typical marking, the position of a marker seen through by the X-ray imaging device 45, and the like are used in this positioning. The treatment radiation irradiation determining device 10 transmits the result of determination to the projection image selecting device 11.

The projection image selecting device 11 selects an image determined to satisfy the treatment radiation irradiation condition by the treatment radiation irradiation determining device 10 and transmits only the selected image to the image reconstructing device 12. The image reconstructing device 12 reconstructs the transmitted images to generate a cone beam CT image in a treatment radiation irradiation state (hereinafter, appropriately called treatment state). The cone beam CT image in the treatment state is transmitted to the patient positioning device 21.

The patient positioning device 21 and the couch control device 22 are a subject positioning control device which measures the amount of displacement in position between a target projected in the first cone beam CT image generated by the first CT image generating apparatus (the treatment radiation irradiation determining device 10, the projection image selecting device 11 and the image reconstructing device 12) and a target projected in the image of the treatment plan, and moves the couch 3 on the basis of the amount of displacement in position therebetween to thereby position the subject 1.

Described more specifically, the patient positioning device 21 displays the cone beam CT image of the treatment state and the CT image of the treatment plan on a display screen. An operator (e.g., a doctor or a medical radiology technician) compares the positions of the target 2 projected in the respective images and confirms whether or not the positions of the target 2 coincide with each other. When the positions of the target 2 coincide with each other or the positional displacement thereof is small, the operator proceeds to the treatment irradiation. When the positions of the target 2 do not coincide with each other, the operator measures the amount of displacement between the two positions. The operator manipulates the patient positioning device 21 to transmit the measured amount of positional displacement to the couch control device 22. The couch control device 22 calculates a control amount for correcting the measured positional displacement amount of the couch driving device 20 and outputs the control amount to the couch driving device 20. The couch driving device 20 moves the couch, on the basis of the control amount to place the target 2 in a planned position. Incidentally, the patient positioning device 21 may measure the amount of positional displacement by means of pattern matching or the like. In this case, the measured amount of positional displacement is preferably automatically transmitted to the couch control device 22.

When the motion tracking treatment mode is selected by the mode switching device 25, the X-ray imaging device 45 performs X-ray imaging from two directions in a state in which the rotatable support device 7 is fixed, to thereby acquire X-ray fluoroscopic images of the subject 1. The target recognizing device 9 recognizes a target projection position from the two images transmitted from the X-ray imaging device 45. The treatment radiation irradiation determining device 10 determines whether or not the transmitted target position satisfies the preset treatment radiation irradiation condition and transmits the result of its determination to the treatment radiation control device 15. The treatment radiation control device 15 controls the treatment radiation irradiating device 8 on the basis of the determination result to irradiate the subject 1 with the controlled treatment radiation therefrom.

Figure 2:
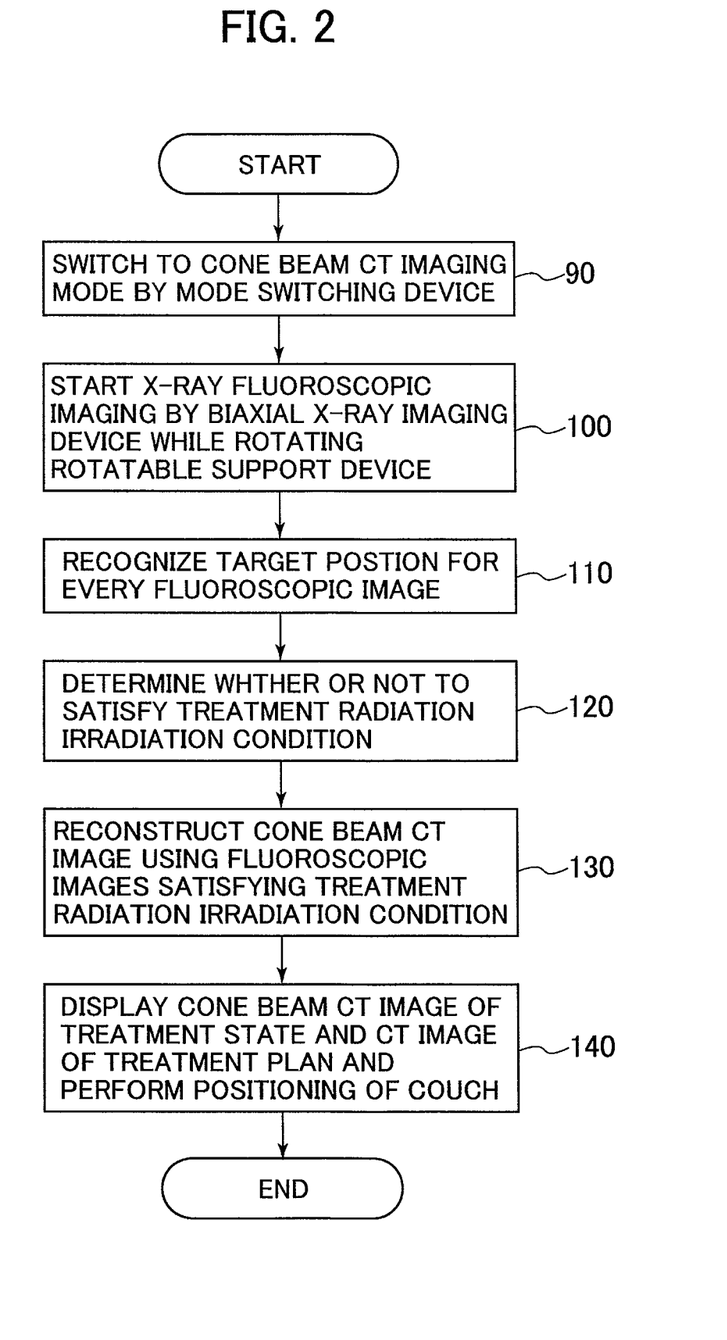
FIG. 2 is a flowchart showing a processing procedure of the radiotherapy system according to the first embodiment of the present invention when the cone beam CT imaging mode is selected and the radiotherapy system is operated as the patient positioning system.

A description will next be made about a processing procedure of the present embodiment where the cone beam CT imaging mode is selected, using FIG. 2. FIG. 2 is a flowchart showing the contents of processing of the above-described target recognizing device 9, treatment radiation irradiation determining device 10, projection image selecting device 11, image reconstructing device 12, rotatable support device control device 13, X-ray imaging control device 14, patient positioning device 21 and couch control device 22.

First, in Step 90, the cone beam CT imaging mode is selected by the mode switching device 25 in accordance with an instruction of the operator.

Thereafter, the flowchart proceeds to Step 100, where the rotation of the rotatable support device 7 and bidirectional X-ray imaging of the X-ray imaging device are started by an instruction of the operator. The imaged X-ray fluoroscopic images are transmitted to the target recognizing device 9.

After that, the flowchart proceeds to Step 110, where the target recognizing device 9 recognizes a target position from the transmitted X-ray fluoroscopic images. This recognition is automatically performed because searching is done by template matching in which the preset X-ray fluoroscopic images of the target 2 are taken as templates. The target recognizing device 9 calculates the three-dimensional position of the target 2 from the target position recognized using each image by three-dimensional backprojection, and transmits information about the three-dimensional position to the treatment radiation irradiation determining device 10 and the projection image selecting device 11. Here, when the similarity in the template matching is lower than the preset threshold, or when the length of a common perpendicular line in the three-dimensional backprojection is lower than the preset threshold, the recognition is judged unsuccessful and the captured images are discarded. Then, the flowchart does not proceed to subsequent Steps and proceeds to the processing of each image captured next.

Thereafter, the flowchart proceeds to Step 120, where the treatment radiation irradiation determining device 10 determines whether or not the transmitted three-dimensional position of the target 2 satisfies the preset treatment radiation irradiation condition, and transmits the result of its determination to the projection image selecting device 11.

Thereafter, the flowchart proceeds to, Step 130, where the projection image selecting device 11 discriminates each image determined to satisfy the treatment radiation irradiation condition and transmits it to the image reconstructing device 12. The image reconstructing device 12 reconstructs the transmitted images to generate a cone beam CT image. The generated cone beam CT image is transmitted to the patient positioning device 21.

Afterwards, the flowchart proceeds to Step 140, where the patient positioning device 21 displays the cone beam CT image of the treatment state and the CT image of the treatment plan on the display screen. When the positions of the target 2 do not coincide with each other, the patient positioning device 21 measures the amount of displacement of the positions and transmits it to the couch control device 22. The couch control device 22 controls the couch driving device 20 to move the couch and places the target 2 in the planned position.

Figure 5A:
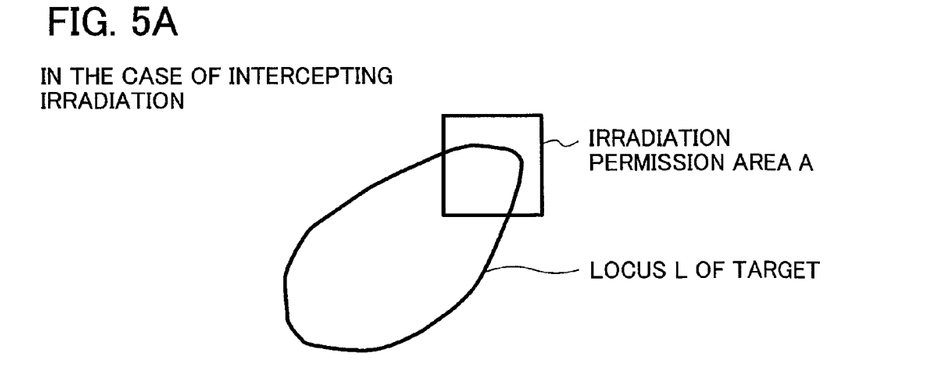
FIG. 5A is a diagram showing a treatment radiation irradiation condition for intercepting irradiation.
Figure 5B:
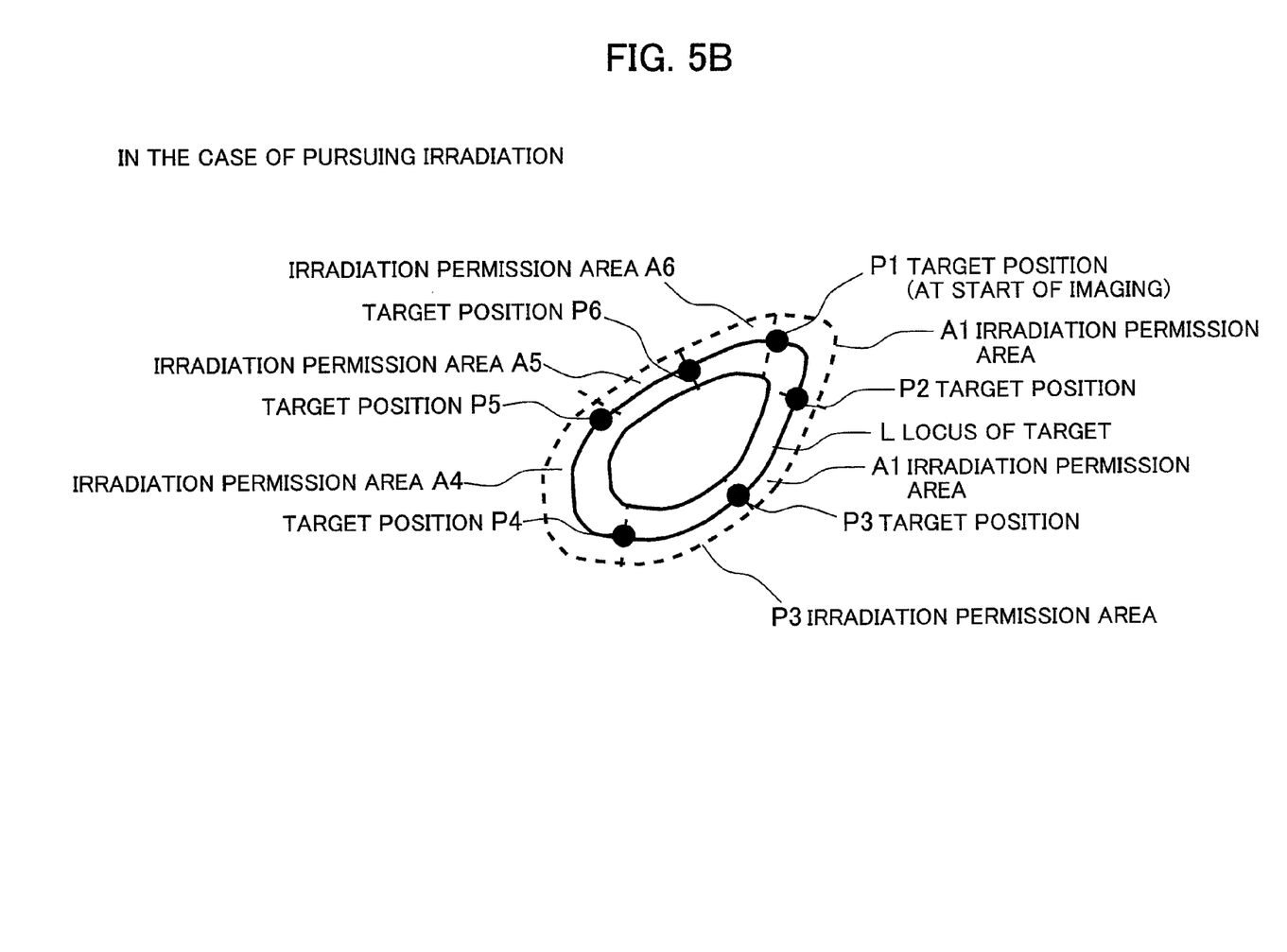
FIG. 5B is a diagram showing a treatment radiation irradiation condition for pursuing irradiation.

A description will be made about treatment radiation irradiation conditions using FIGS. 5A and 5B. FIG. 5A is a diagram showing a treatment radiation irradiation condition for intercepting irradiation, and FIG. 5B is a diagram showing a treatment radiation irradiation condition for pursuing irradiation.

When an irradiation target 2 such as an affected part is moved due to respiration or the like, it becomes difficult to form a preplanned dose distribution. In such a case, there are provided intercepting irradiation and pursuing irradiation using a motion tracking device as a method for accurately applying radiation onto the target 2 to form the preplanned dose distribution. The intercepting irradiation is a method for performing irradiation only when the target 2 is placed in a prescribed position (emission permission area). The pursuing irradiation is a method for changing the direction of treatment radiation according to the movement of the target 2 to perform irradiation thereof. The pursuing irradiation also needs to stop the irradiation of radiation where the target 2 is moved to a position where an internal organ, a bone or the like exists in front of the target 2 as seen in the irradiation direction.

In FIG. 5A, L is a locus of the target 2 of the treatment plan, and A is an irradiation permission area for intercepting irradiation. The irradiation permission area A is a treatment radiation irradiation condition. Only when the target 2 is within the irradiation permission area A, radiation is applied. Upon imaging of the cone beam CT in the present embodiment, the irradiation permission area A is used, images in which a target position lies in the irradiation permission area A (which satisfy the treatment radiation irradiation condition) are selected, and image reconstruction is performed using only those images. It is thus possible to bring a patient lying in a state (treatment radiation irradiated state) of being irradiated with a treatment beam in the irradiation permission area A into three-dimensional CT imaging (visualization). Here, the irradiation permission area may be set divided into a plurality of areas. A cone beam CT image may be reconstructed with respect to each irradiation permission area.

In the case of the pursuing irradiation, upon the treatment plan, target positions are acquired along the locus L of the target 2 at predetermined time intervals from the start of imaging. Black circles in FIG. 5B are the acquired target positions. The black circle P1 indicates the target position at the start of imaging in the treatment plan, and the black circles P2 to P6 indicate the target positions taken along the subsequent locus L. Next, an area that causes the locus L of the target 2 to have a preset width (e.g., ±2 mm) is set between the target positions P1 and P2. This is referred to as an irradiation permission area A1. Subsequently, in the same manner as above, irradiation permission areas A2 to A6 are set. This setting is continued until the target 2 returns to the irradiation permission area A1.

In the pursuing irradiation, when the direction of the treatment radiation is changed according to the movement of the target 2 to perform its irradiation, the radiation is applied only where the target 2 is in the irradiation permission areas A1 to A6. The irradiation permission areas A1 to A6 correspond to the treatment radiation irradiation conditions. Upon the imaging of the cone beam CT in the present embodiment, the irradiation permission areas A1 to A6 are used, and an image (which satisfies the treatment radiation irradiation condition) in which each of target positions is in each of the irradiation permission areas A1 to A6 is selected, followed by image reconstruction using only the selected images. It is thus possible to visualize a patient held in a state (treatment radiation irradiated state) of being irradiated with a treatment beam in the irradiation permission areas A1 to A6. Although the target positions are set to P1 to P6 herein, the target positions may be divided by an arbitrary number. Further, the irradiation permission areas A1 to A6 are set identical to the number of the target positions, but they may be increased or decreased to an arbitrary number.

According to the present embodiment as described above, the image in which the position of the target recognized by the target recognizing device 9 satisfies the treatment radiation irradiation condition for the motion tracking treatment is selected out of the X-ray images acquired by the X-ray imaging device 45 to generate the cone beam CT image (first cone beam CT image), so that the subject 1 being in treatment radiation irradiated state can be brought into the three-dimensional CT imaging (visualization). It is thus possible to acquire the image that enables to grasp the positional relationship of the target in the treatment radiation irradiated state, the passing area of radiation, and the critical organ, which are necessary for the positioning of the patient for radiation treatment. As a result, the accurate patient positioning as in the treatment plan is possible and a motion tracking treatment good in accuracy becomes possible.

Incidentally, although the above-described embodiment has described the example in which when the target recognizing device 9 recognizes the target 2, it directly searches the target 2 from the images by the image recognition processing, an alternate marker can be caused to enter the neighborhood of the target 2, and the target position may be estimated from the position of the alternate marker using this alternate marker. A golden spherical marker is used as the alternate marker. Since projection images in arbitrary directions are identical in the case where the marker is spherical, the target 2 can be recognized by the same templates upon the above template matching. Further, in the present embodiment, the X-ray imaging device taking the form of two pairs has been used, but an X-ray imaging device taking the form of one pair may be used.

Second Embodiment

A second embodiment of the present invention will be described using FIGS. 3A, 3B and 4.

Figure 3A:
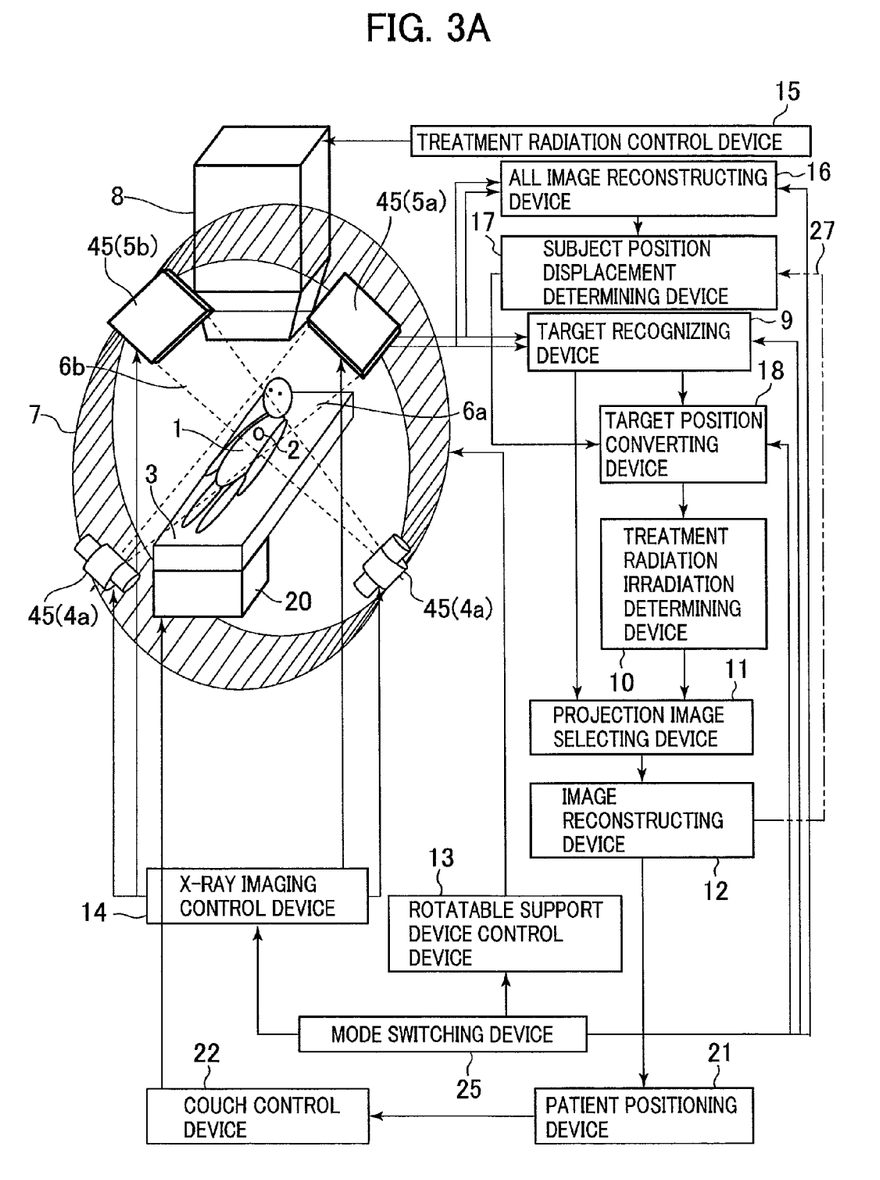
FIG. 3A is a diagram showing a schematic configuration of a radiotherapy system according to a second embodiment of the present invention, and a diagram showing a state when a cone beam CT imaging mode is selected and the radiotherapy system is operated as a patient positioning system.
Figure 3B:
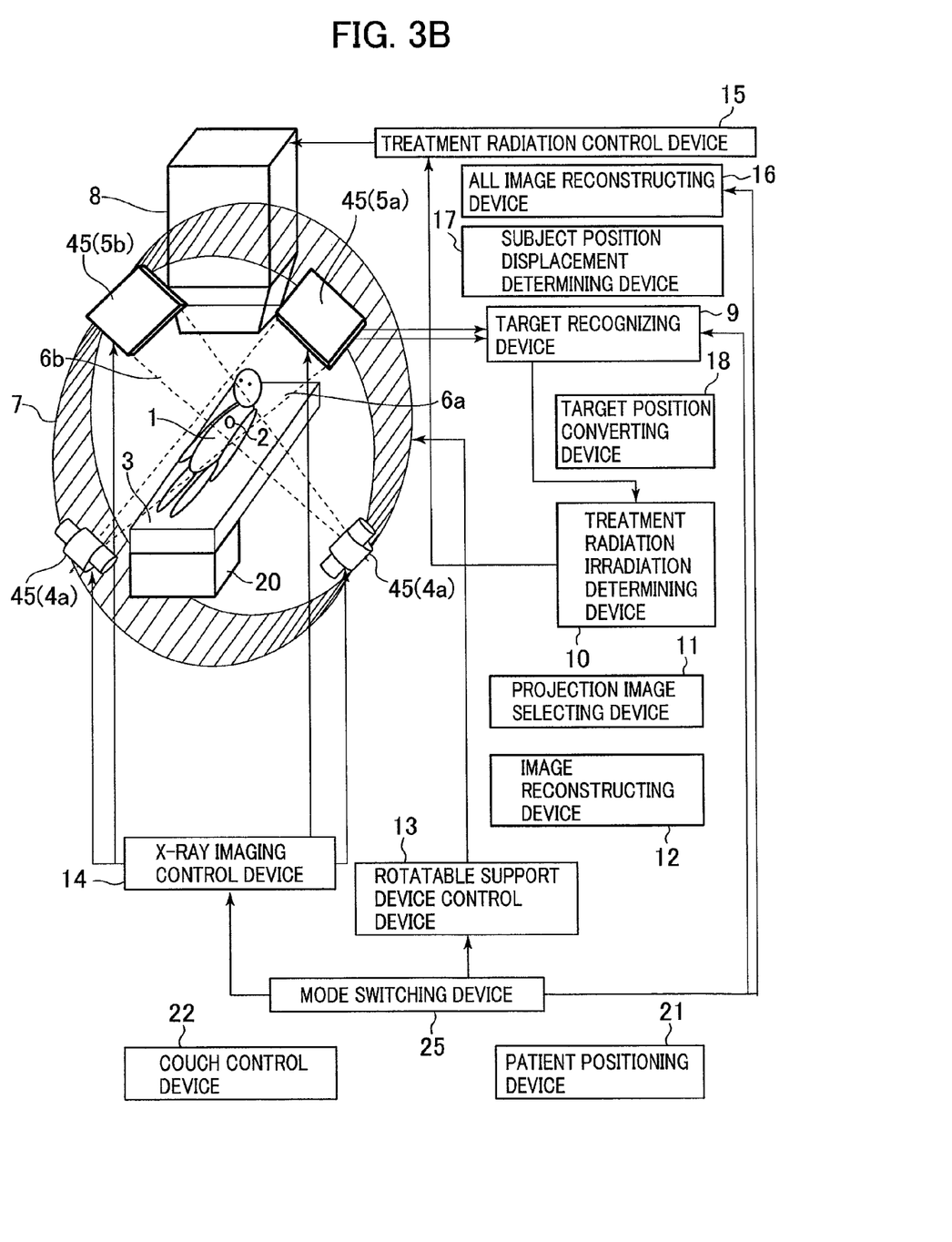
FIG. 3B is a diagram showing the schematic configuration of the radiotherapy system according to the second embodiment of the present invention, and a diagram showing a state when a motion tracking treatment mode is selected and the radiotherapy system is operated as a motion tracking treatment system.
Figure 4:
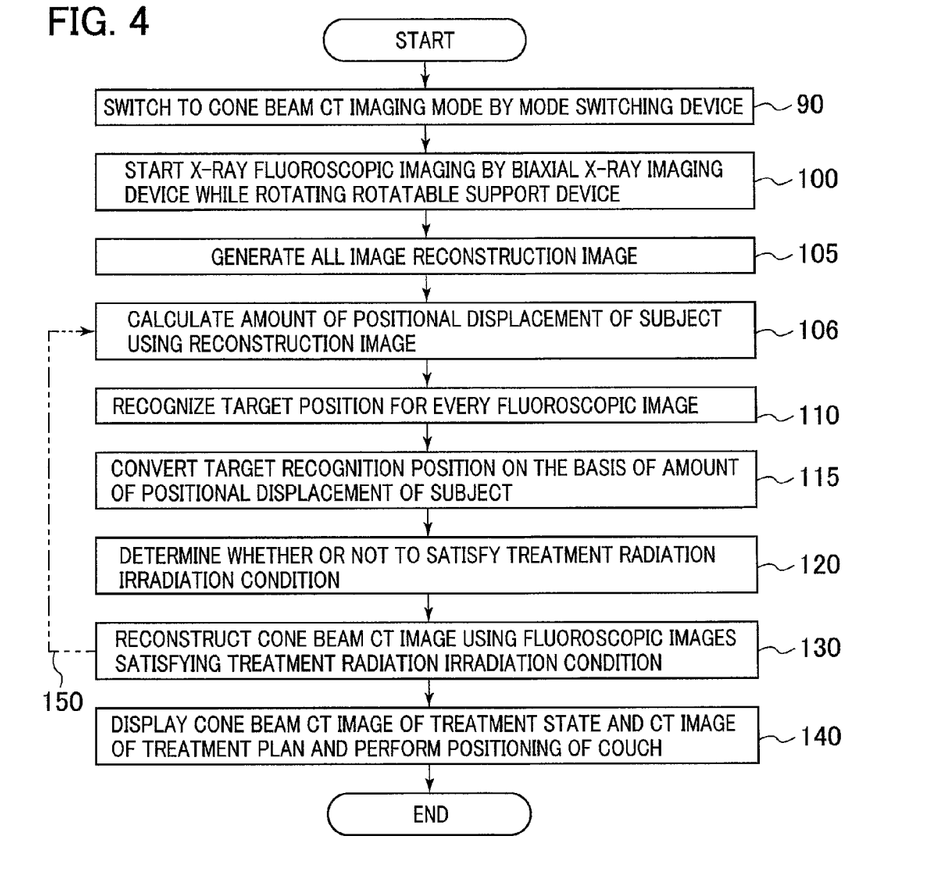
FIG. 4 is a flowchart showing a processing procedure of the radiotherapy system according to the first embodiment of the present invention when the cone beam CT imaging mode is selected and the radiotherapy system is operated as the patient positioning system.

FIGS. 3A and 3B are diagrams showing a schematic configuration of a radiotherapy system according to the second embodiment of the present invention, in which FIG. 3A shows a state when a cone beam CT imaging mode is selected and the radiotherapy system is operated as a patient positioning system, and FIG. 3B shows a state when a motion tracking treatment mode is selected and the radiotherapy system is operated as a motion tracking treatment system.

The present embodiment is an example of a radiotherapy system that enables not only cone beam CT imaging of a subject in a treatment state but also coarse positioning of the subject prior to the cone beam CT imaging on software (arithmetic processing).

In FIGS. 3A and 3B, the radiotherapy system according to the present embodiment has an all image reconstructing device 16 (second CT image generating apparatus), a subject positional displacement determining device 17 (first subject positional displacement amount determining device) and a target position converting device 18 (first target position correcting device) in addition to the system configuration shown in FIGS. 1A and 1B.

When a cone beam CT imaging mode is selected by the mode switching device 25, a target 2 in a subject 1 located on a couch 3 is imaged from two directions by the two pairs of X-ray tubes 4a, 4b and X-ray detectors 5a, 5b while rotating the rotatable support device 7 as with the first embodiment. The captured projection images are transmitted to the target recognizing device 9 and transmitted even to the all image reconstructing device 16.

The all image reconstructing device 16 performs image reconstruction using all images transmitted thereto. Consequently, an all image cone beam CT image is obtained in which the movements of the subject 1 during its imaging are all added together. The all image cone beam CT image is transmitted to the subject positional displacement determining device 17.

The patient positional displacement determining device 17 determines the amount of positional displacement of the subject by referring to a reference image recorded in advance. A CR image or the like used in the treatment plan is used as for the reference image. Positioning is highly accurately possible between three-dimensional images. Since, however, an organ moved due to respiration or the like is in a displaced state, reference is made to an organ, e.g., a bone structure or the like that moves little. It is thus possible to determine the amount of displacement of the subject from the position thereof in its treatment plan. The determined amount of displacement is transmitted to the target position converting device 18.

The target position converting device 18 adds the amount of displacement of the subject obtained by the patient positional displacement determining device 17 to the coordinate value of a target position obtained by the target recognizing device 9 to thereby convert the coordinate value of the target position obtained by the target recognizing device 9 into a coordinate value after the movement of the subject. It is thus possible to obtain a target position at the position of the subject positioned precisely using the cone beam CT image without actually moving the patient and re-imaging it. The converted coordinate value is transmitted to the treatment radiation irradiation determining device 10.

The treatment radiation irradiation determining device 10, the projection image selecting device 11 and the image reconstructing device 12 select projection images on the basis of the target position transmitted in a manner similar to the first embodiment and performs image reconstruction to thereby generate a cone beam CT image. The patient positioning device 21 and the couch control device 22 control the couch driving device 20 on the basis of the generated cone beam CT image of treatment state and the CT image of the treatment plan to move the couch and thereby place the target 2 in the planned position.

By the above system, both of the previous coarse positioning of the subject using the normal cone beam CT and the cone beam CT imaging of the treatment state for the precise subject positioning can be performed by one X-ray fluoroscopic imaging.

That is, a three-dimensional CT image in a state in which the subject is visually coarsely positioned by an operator, is obtained by the all image reconstruction in the all image reconstructing device 16. Referring to the three-dimensional CT image, the amount of positional displacement relative to the position of the treatment plan is calculated on the basis of a portion such as the backbone that moves little. This becomes coarse positioning data for the cone beam CT imaging in the treatment state.

Here, if the patient is actually moved to retake a CT image, the locus of the target 2 at that time coincides with that of the treatment plan. It is therefore possible to select the images coincident with that at the treatment on the basis of the irradiation permission area and perform image reconstruction using them (first embodiment). It is however not desirable to perform the two CT imaging because the radiation exposure dose increases. Thus, the target position after the movement of the couch is determined on the basis of the amount of displacement of the patient relative to the position at the treatment plan without actually moving the patient and re-imaging the same. It is determined whether or not the target 2 enters the irradiation permission area at the target position after the movement of the patient. The image reconstruction is performed on the basis of the image in which the target 2 enters the irradiation permission area. At last, detailed patient positioning is performed using the cone beam CT image of the treatment state reconstructed using the image in which the target 2 enters the irradiation permission area.

Thus, according to the present embodiment, it is possible to perform on the software (arithmetic processing) not only the cone beam CT imaging of the subject 1 being in the treatment state but also the coarse positioning of the subject 1 prior to the cone beam CT imaging. High-accuracy positioning becomes possible compared with the conventional coarse positioning before the cone beam CT imaging performed using the marking on the surface of the subject or the position of the marker seen through by the X-ray imaging device, etc.

Further, although the amount of displacement of the subject is determined using the all image cone beam CT image in the above procedure, the amount of displacement of the subject can be recalculated again using the cone beam CT image of the treatment state obtained by the above procedure, followed by transmission to the target position converting device 9, and the cone beam CT image of the treatment state may be reconstructed again.

In this case, a signal line 27 indicated by an imaginary line in FIG. 3A is added as a control flow. The subject positional displacement determining device 17 configures a second subject positional displacement amount determining device which compares the first cone beam CT image generated by the first CT image generating apparatus (the treatment radiation irradiation determining device 10, the projection image selecting device 11 and the image reconstructing device 12) and the image of the treatment plan to determine the amount of positional displacement of the subject 1. The target position converting device 18 configures a second target position correcting device which corrects the position of the target recognized by the target recognizing device 9, on the basis of the amount of positional displacement of the subject 1 determined by the second subject positional displacement amount determining device. The first CT image generating apparatus (the treatment radiation irradiation determining device 10, the projection image selecting device 11 and the image reconstructing device 12) selects an image in which the position of the target corrected by the second target position correcting device satisfies the treatment radiation irradiation condition for motion tracking treatment, out of X-ray images acquired by the X-ray imaging device 45 to perform image reconstruction on the basis of it, thereby generating a new cone beam CT image. This enables the generation of the cone beam CT image in a state in which the whole subject 1 is closer to the treatment state (this will be described later).

The operation of selecting the motion tracking treatment mode by the mode switching device 25 is identical to the first embodiment shown in FIG. 1B as shown in FIG. 3B.

A description will next be made about a processing procedure of the present embodiment where the cone beam CT imaging mode is selected, using FIG. 4. FIG. 4 is a flowchart showing the contents of processing of the above-described target recognizing device 9, treatment radiation irradiation determining device 10, projection image selecting device 11, image reconstructing device 12, rotatable support device control device 13, X-ray imaging control device 14, patient positioning device 21, couch control device 22, all image reconstructing device 16, subject positional displacement determining device 17 and target position converting device 18.

In addition to the flowchart of FIG. 2 showing the processing procedure of the first embodiment, Step 105 for generating all image reconstruction image, and Step 106 for calculating the amount of positional displacement of the subject using the all image reconstruction image are appended after Step 100. Further, Step 115 for converting the target position recognized in Step 110 to a coordinate value after the correction of the amount of positional displacement of the subject on the basis of the amount of positional displacement of the subject calculated in Step 106 is appended. A cone beam CT image of a treatment state is generated by Steps 120, 130 and 140 as with the first embodiment on the basis of the converted target position, and hence precise positioning of the subject is performed.

As described above, the amount of positional displacement of the subject may be recalculated from Step 106 on the basis of the cone beam CT image of the treatment state generated in Step 130. This is a loop indicated by reference numeral 150, which is returned from Step 130 to Step 106.

Since the three-dimensionally reconstructed CT image is used in the first calculation (coarse positioning) of the amount of positional displacement of the subject, the organ moved due to respiration is displaced, and the amount of positional displacement is calculated on the basis of the portion such as the unmoved backbone. Since, however, the cone beam CT image of the treatment state obtained in Step 130 has no displacement over all organs, the amount of positional displacement of the subject can be calculated more highly accurately (coarse positioning). If the coarse positioning position is more coincident with the treatment plan, a determination as to whether or not the target 2 is in the irradiation permission area becomes more accurate. Thus, a higher precision cone beam CT image of a treatment state is obtained, and more detailed patient positioning can be performed using the cone beam CT image.

What is claimed is:

1. A radiotherapy system comprising:
   a couch for supporting a subject;
   a rotatable support device disposed around the couch;
   a treatment radiation irradiating device attached to the rotatable support device;
   a treatment radiation control device that controls the treatment radiation irradiating device to irradiate the subject when a position of a target in the subject satisfies a treatment radiation irradiation condition of a treatment plan for motion tracking treatment of the target;
   an X-ray imaging device to perform X-ray imaging which is attached to the rotatable support device and which includes two separate X-ray tubes which apply X-rays to the subject from a plurality of directions while rotating around the subject and two separate X-ray detectors which acquire a plurality of pairs of bidirectional X-ray images corresponding to the applied X-rays;
   a target recognizing device that recognizes a three-dimensional position of the target in the subject from each of the pairs of bidirectional X-ray images acquired by the X-ray imaging device; and
   a first CT image generating apparatus configured to:
   select, out of the bidirectional X-ray images acquired by the X-ray imaging device, ones of the bidirectional X-ray images in which the three-dimensional position of the target recognized by the target recognizing device satisfies the treatment radiation irradiation condition for the motion tracking treatment of the target, and
   perform image reconstruction on the selected ones of the bidirectional X-ray images to generate a first cone beam CT image.

2. The radiotherapy system according to claim 1, wherein the treatment radiation irradiation conditions are set for a plurality of positions, and said first CT image generating apparatus selects ones of the X-ray images in which the position of the target satisfies the respective set conditions for the plural positions and generates a plurality of reconstructed cone beam CT images.

3. The radiotherapy system according to claim 1, further comprising:
   a subject positioning control device configured to:
   measure an amount of displacement in position between the target projected in the first cone beam CT image generated by the first CT image generating apparatus and the target projected in an image of the treatment plan,
   move the couch on the basis of the measured amount of positional displacement, and
   position the subject on the basis of the measured amount of positional displacement.

4. The radiotherapy system according to claim 1, wherein the treatment radiation control device applies radiation for the motion tracking treatment on the basis of the position of the target recognized by the target recognizing device.

5. The radiotherapy system according to claim 1, wherein the target recognizing device searches for a marker installed on the target or on the couch by image recognition processing of the X-ray images acquired by the X-ray imaging device to determine a three-dimensional coordinate of the target.

6. The radiotherapy system according to claim 1, wherein:
   the subject is coarsely positioned on the couch in advance using a marker placed on the surface of the subject or seen through the subject by the X-ray imaging device, and
   the X-ray imaging device acquires the X-ray images of the coarsely positioned subject.

7. A radiotherapy system, further comprising:
   a couch for supporting a subject;
   a rotatable support device disposed around the couch;
   a treatment radiation irradiating device attached to the rotatable support device;
   a treatment radiation control device that controls the treatment radiation irradiating device to irradiate the subject when a position of a target in the subject satisfies a treatment radiation irradiation condition of a treatment plan for motion tracking treatment of the target;
   an X-ray imaging device to perform X-ray imaging which is attached to the rotatable support device and which includes two separate X-ray tubes which apply X-rays to the subject from a plurality of directions while rotating around the subject and two separate X-ray detectors which acquire a plurality of X-ray images corresponding to the applied X-rays;
   a target recognizing device that recognizes a three-dimensional position of the target in the subject from each of the X-ray images acquired by the X-ray imaging device;
   a first CT image generating apparatus that performs image reconstruction using each of the X-ray images acquired by the X-ray imaging device to generate a first cone beam CT image;
   a first subject positional displacement amount determining device that determines an amount of positional displacement of the subject from the first cone beam CT image and an image of the treatment plan;
   a first target position correcting device that corrects the position of the target recognized by the target recognizing device on the basis of the amount of positional displacement determined by the first subject positional displacement amount determining device; and
   a second CT image generating apparatus configured to:
   select, out of the X-ray images acquired by the X-ray imaging device, ones of the X-ray images in which the three-dimensional position of the target corrected by the first target position correcting device satisfies the treatment radiation irradiation condition for the motion tracking treatment of the target,
   perform image reconstruction on the selected ones of the X-ray images, and
   generate a second cone beam CT image.

8. The radiotherapy system according to claim 7, further comprising:
   a second subject positional displacement amount determining device that compares the second cone beam CT image generated by the second CT image generating apparatus and the image of the treatment plan to determine an amount of positional displacement of the subject, and a second target position correcting device that corrects the position of the target recognized by the target recognizing device on the basis of the amount of positional displacement determined by the second subject positional displacement amount determining device, wherein the first CT image generating apparatus is further configured to:

select, out of the X-ray images acquired by the X-ray imaging device, ones of the X-ray images in which the three-dimensional position of the target corrected by the second target position correcting device satisfies the treatment radiation irradiation condition for the motion tracking treatment of the target,     perform image reconstruction on the selected ones of the X-ray images, and     generate a third cone beam CT image.

\* \* \* \* \*